United States Patent [19]
Ernst et al.

[11] Patent Number: 5,625,099
[45] Date of Patent: Apr. 29, 1997

[54] PREPARATION OF ASTAXANTHIN, NOVEL INTERMEDIATES THEREFOR AND THE PREPARATION THEREOF

[76] Inventors: Hansgeorg Ernst, Bussardweg 62, 67346 Speyer; Walter Dobler, Liebermannstrasse 23, 69126 Heidelberg; Joachim Paust, Ringstrasse 3, 67141 Neuhofen; Udo Rheude, Wildentenstrasse 1, 67166 Otterstadt, all of Germany

[21] Appl. No.: 471,314

[22] Filed: May 23, 1995

Related U.S. Application Data

[62] Division of Ser. No. 265,741, Jun. 27, 1994, Pat. No. 5,455,362.

[30] Foreign Application Priority Data

Jul. 5, 1993 [DE] Germany ............ 43 22 277.3

[51] Int. Cl.$^6$ ............................................. C07C 45/45
[52] U.S. Cl. .................. 568/347; 568/345; 568/343; 568/361; 568/11
[58] Field of Search .................. 549/437, 214; 568/347, 345, 343, 361, 11

[56] References Cited

U.S. PATENT DOCUMENTS

| | | | |
|---|---|---|---|
| 4,245,109 | 1/1981 | Mayer et al. | 560/61 |
| 4,283,559 | 8/1981 | Broger et al. | 568/11 |
| 4,585,885 | 4/1986 | Bernhard et al. | 566/436 |
| 5,210,314 | 5/1993 | Ernst et al. | 568/345 |

FOREIGN PATENT DOCUMENTS 005748  12/1979  European Pat. Off. .

OTHER PUBLICATIONS

Widmer et al., Chem. Abst., 96: 85791p (1982).
Widmer et al., Helv. Chim. Acta 64, 2436–2446 (1981).
Rosenberger et al., J. Org. Chem., 47, 2130–2134 (1982).

*Primary Examiner*—Nicky Chan

[57] ABSTRACT

Abstract of the Disclosure: Compounds of the formula I

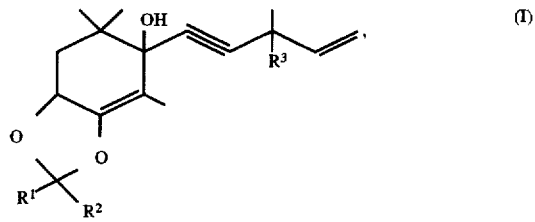

where $R^1$ is H or $C_1$–$C_4$-alkyl, $R^2$ is $C_1$–$C_4$-alkyl and $R^3$ is an ether, silyl ether or acetal protective group which can be converted into a hydroxyl group by hydrolysis, in particular one of the radicals

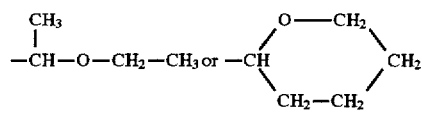

and a process for preparing these compounds by reacting an alkenyne of the formula II

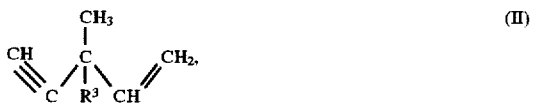

in an inert solvent in the presence of lithium amide with a cyclohexenone of the formula III

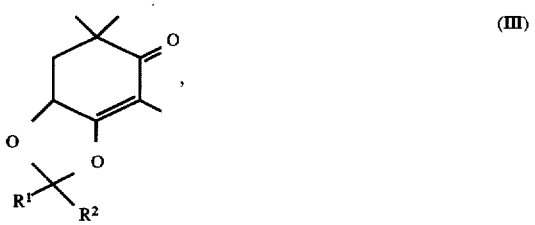

and the use of the compounds of the formula I for preparing astaxanthin, are described.

2 Claims, No Drawings

PREPARATION OF ASTAXANTHIN, NOVEL INTERMEDIATES THEREFOR AND THE PREPARATION THEREOF

This is a Division of application Ser. No. 08/265,741, filed Jun. 27, 1994, now U.S. Pat. No. 5,455,362.

The present invention relates to compounds of the formula I

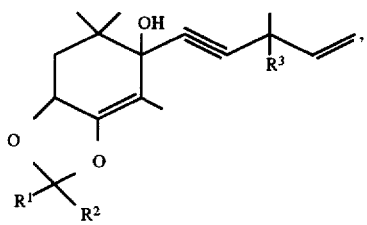
(I)

where $R^1$ is H or $C_1$–$C_4$-alkyl, $R^2$ is $C_1$–$C_4$-alkyl and $R^3$ is an ether, silyl ether or acetal protective group which can be converted into a hydroxyl group by hydrolysis, preferably one of the radicals

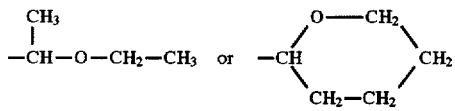

to the preparation thereof and to the use thereof for preparing astaxanthin and other essential astaxanthin precursors.

The $C_{40}$-carotenoid astaxanthin of the formula V

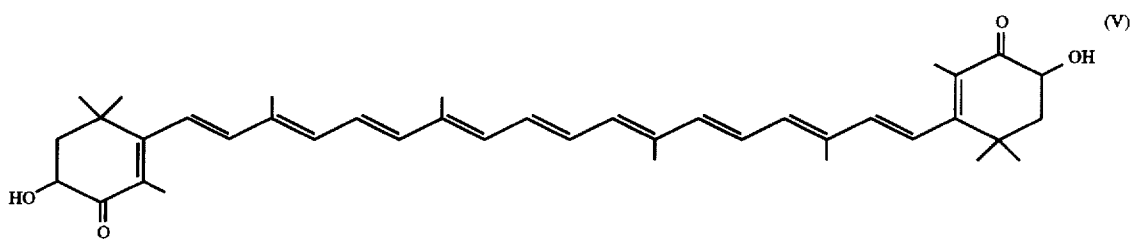
(V)

is a dye which is in demand for fish pigmentation. The possibilities of isolating astaxanthin from natural sources, such as algae or yeasts, are limited. There has thus been no lack of attempts to prepare astaxanthin by synthesis.

One astaxanthin synthesis which can be implemented industrially is described in EP 5748 and in Helv. Chim. Acta 64 (1981) 2436 et seq. The synthetic scheme for this is as follows:

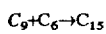

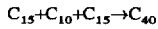

The $C_9$ unit employed in each case is 2,2,4,6,6-pentamethyl-7,7a-dihydro-2H, 6H-1,3-benzodioxol-5-one which can be prepared from 3,4-dihydroxy-2,6,6-trimethyl-2-cyclo-hexen-1-one by reaction with acetone or 2,2-dimethoxypropane:

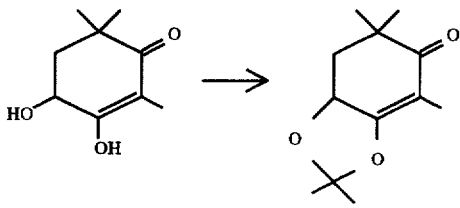

The $C_6$ unit mentioned in the said references is 3-methylpentenyn-1-ol of the formula

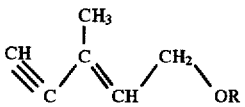

with protected OH group. Protective groups mentioned besides the trialkylsilyl group are the tert-butyl group and the —C(CH$_3$)$_2$—O—CH$_3$ group. EP 5748 additionally mentions as $C_6$ unit the trialkylsilyl ether of 3-methylpentenyn-3-ol of the formula

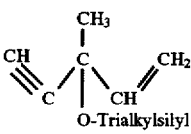

No experimental examples of the reaction of this 3-methylpentenyn-3-ol ether with the $C_9$ unit are given. The key step in the synthesis is the linkage of the $C_9$ unit to a $C_6$ unit by means of an organometallic reaction. The acetylene is deprotonated using either a Grignard reagent in tetrahydrofuran (THF) or a butyllithium solution. The Grignard variant and the butyllithium variant are systematically compared in Helv. Chim. Acta 64 (1981) 2439, and the butyllithium variant is unambiguously preferred. The yield of the coupled product in this case was 85.6% of theory.

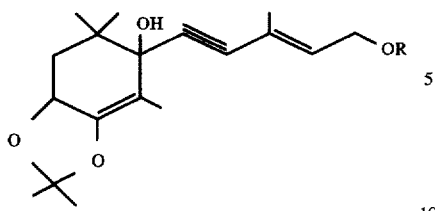

All the protective groups are eliminated from this coupled product on workup in mineral acid medium to form 6-hydroxy-3-(3-methyl-5-hydroxy-3-penten-1-ynyl)-2,4,4-trimethyl-2-cyclohexenone. It is possible to prepare from this, by reducing the triple bond with zinc dust and acetic acid in $CH_2Cl_2$ and subsequently reacting with HBr and then with triphenylphosphine, a $C_{15}$-triphenylphosphonium salt which can be reacted with 2,7-dimethyl-2,4,6-octatrienedial to give astaxanthin.

The process is intrinsically very good but has the disadvantage of the necessity to use butyllithium, which is very costly, flammable and not easy to handle industrially. In addition, the butyllithium is generally in the form of a solution in hexane so that it would be necessary, after the reaction, to work up a mixture of organic solvents.

The use of a Grignard reagent is also not very advantageous industrially because of difficulties in handling the low-boiling alkyl halides and because of possible technical problems with the preparation of the Grignard reagent (initiation of the reaction).

It is an object of the present invention to improve the known synthesis of astaxanthin to avoid the prior art disadvantages in the linkage of the $C_9$ unit to a $C_6$ unit.

We have found that this object is achieved by linking the $C_9$ unit to an appropriate $C_6$ unit under conditions which are industrially much simpler, namely in an organic solvent in the presence of lithium amide in place of butyllithium or a Grignard reagent, when the $C_6$ unit is a derivative of 3-methylpentenyn-3-ol of the formula II

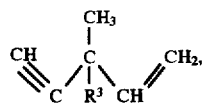
(II)

where $R^3$ is an ether, silyl ether or acetal protective group which can be converted into a hydroxyl group by hydrolysis, in particular one of the radicals

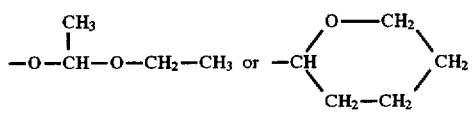

This reaction results in formation of the compounds of the formula I which have not been described in the literature.

The smoothness of this reaction is particularly surprising because when the $C_6$ unit with the ether group in position 1, of the formula

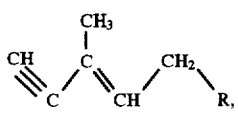

where R is

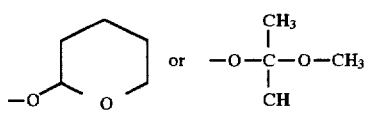

was used as starting material in methyl tert-butyl ether, no reaction with the $C_9$ unit was detectable.

The invention therefore also relates to a process for preparing compounds of the formula I

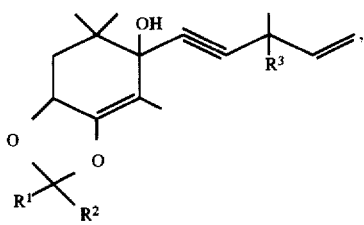
(I)

where $R^1$ is H or $C_1$-$C_4$-alkyl, $R^2$ is $C_1$-$C_4$-alkyl and $R^3$ is an ether, silyl ether or acetal protective group which can be converted into a hydroxyl group by hydrolysis, which comprises reacting an alkenyne of the formula II

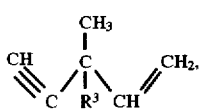
(II)

where $R^3$ has the abovementioned meaning, in an inert solvent in the presence of lithium amide with a cyclohexenone of the formula III

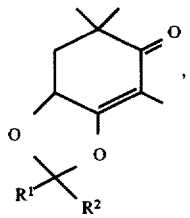
(III)

where $R^1$ and $R^2$ have the abovementioned meanings.

Preferred $C_9$ units are cyclohexenones of the formula III where $R^1$ is H or methyl and $R^2$ is methyl. The cyclohexenone of the formula III with $R^1$=H and $R^2$=methyl has not been described in the literature. It can be obtained by reacting 3,4-dihydroxy-2,6,6-trimethyl-2-cyclohexen-1-one with vinyl ethyl ether. The reaction of this $C_9$ unit with an alkenyne of the formula II where $R^3$ is —O—CH($CH_3$)—O—$CH_2$-$CH_3$ is industrially and economically particularly advantageous because bothunits are prepared with the same supplier of protective groups, with vinyl ethyl ether. This alkenyne has been disclosed in J. Org. Chem. 4,? (1982) 2130 - 2134. According to loc. cit., in a canthaxanthin synthesis it is metallated with butyl-lithium and then linked to 2,6,6-trimethyl-2-cyclohexenone.

Protective groups which are suitable for the alkenynes of the formula II are those which can be relatively easily converted into the hydroxyl group by hydrolysis. Examples which may be mentioned are ether groups such as

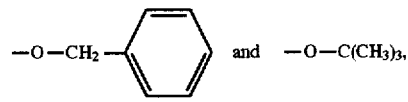

silyl ether groups such as —O—Si($CH_3$)$_3$ or acetal groups such as the α-alkoxyalkyl ether groups of the formulae

—O—CH₂—O—CH₃,

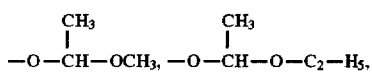

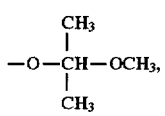

and suitable pyranyl ether groups such as the tetrahydropyranyloxy group and the 4-methyl-5,6-dihydro-2H-pyranyloxy group.

It is particularly advantageous to use alkenynes of the formula II where $R^3$ is the tetrahydropyranyloxy group

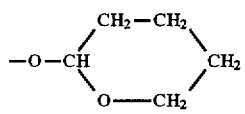

or the α-ethoxyethoxy group of the formula

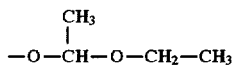

The alkenynes of the formula II are generally used in an excess of from 0 to 100 mol %, preferably 50 to 75 mol %, based on the $C_9$ units of the formula III.

Inert solvents suitable for the process according to the invention are in general solvents which are inert to lithium amide. It is advantageous to use an ethereal solvent such as dialkyl ethers, tetrahydrofuran or dioxane, especially methyl tert-butyl ether which is immiscible with water.

The lithium amide is generally used in amounts of from 1.0 to 1.05, preferably about 1.02, equivalents based on the alkenyne of the formula II.

The process is generally carried out by suspending solid lithium amide in the inert solvent and slowly adding to this suspension the alkenyne of the formula II, the latter being deprotonated by the lithium amide. The $C_9$ unit of the formula III is run into the resulting suspension of the lithium alkenyne. After reaction has continued for several hours, water is added for hydrolysis. When methyl tert-butyl ether is used as solvent, the required product of the formula I is present in the upper organic phase, which greatly simplifies the industrial implementation of the process. It can be isolated in a yield of about 95% by removing the solvent and any excess $C_6$ unit by distillation. The distilled $C_6$ unit can be returned to the synthesis without difficulty.

It was surprising that it is possible to carry out the reaction of the cyclohexenone of the formula III with the alkenyne of the formula II so advantageously in an inert organic solvent because in the prior art for example it was necessary to react 6-oxoisophorone of the formula

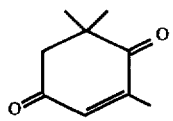

with an alkenyne at −40° C. and in liquid ammonia when a lithium amide was used (cf. Helv. Chim. Acta 6.5. (1982) No. 89, 958–967, especially 960), which is industrially very elaborate and costly.

The temperatures for the described linkage reaction are generally from room temperature to the boiling point of the solvent.

Elimination of protective groups from compounds of the formula I according to the invention in aqueous acidic medium gives 6-hydroxy-3-(3-hydroxy-3-methyl-4-penten-1-ynyl)-4,4,6-trimethyl-2-cyclohexen-1-one of the formula VI

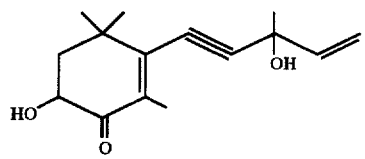

(VI)

in virtually quantitative yield. This alkynediol of the formula VI is known from the process disclosed in Helv. Chim. Acta 65 (1982) 671 et seq., in which it was obtained in a yield of only 56.2% despite the use of butyllithium for the linkage. The alkynediol of the formula VI can be reduced with zinc dust and acetic acid in a chlorohydrocarbon such as methylene chloride or in other inert organic solvents such as methyl tert-butyl ether or toluene or else in glacial acetic acid to the $C_{15}$-diol of the formula IV

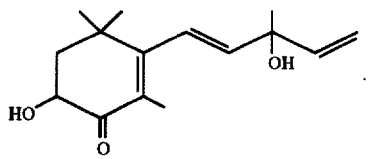

(IV)

The reduction of the alkynediol of the formula VI with zinc/acetic acid has not been described in the literature.

It is preferable to use an approximately 20% strength solution of the alkynediol of the formula VI in methylene chloride/glacial acetic acid, using the latter in the ratio of about 1:2 to 1:2.5. The zinc is expediently used in an amount of about 1 to 3 gram atoms, preferably about 1.3 to 1.5 gram atoms per mole of starting material. The temperatures for this hydrogenation are from −20° C. to room temperature, preferably about The $C_{15}$-diol of the formula IV obtained in this way can then be converted into astaxanthin, advantageously as described in Helv. Chim. Acta 64 (1981) 2419–2446. We have also found that the synthesis of astaxanthin starting from the alkynediol of the formula VI can also be carried out without intermediate isolation of the $C_{15}$-diol of the formula IV, of the $C_{15}$-bromide of the formula VII prepared therefrom or of the $C_{15}$-triphenylphosphonium salt of the formula VIII prepared therefrom, ie. virtually in a one-pot reaction. This provides further great advantages compared with the prior art synthesis of astaxanthin.

The invention therefore also relates to a very advantageous overall process for preparing astaxanthin of the formula V, which comprises A. reacting an alkenyne of the formula II

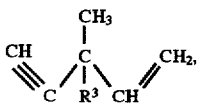

(II)

where $R^3$ is an ether, silyl ether or acetal protective group which can be converted into a hydroxyl group by hydrolysis, in an inert solvent in the presence of lithium amide with a cyclohexenone of the formula III

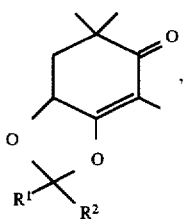

(III)

where $R^1$ is H or $C_1$–$C_4$-alkyl and $R^2$ is $C_1$–$C_4$-alkyl,

B. eliminating from the resulting compound of the formula I

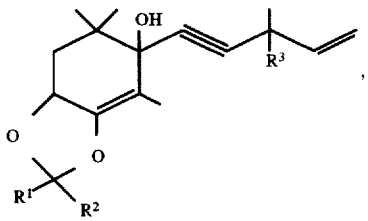

(I)

the protective groups in aqueous acidic medium,

C. reducing the resulting alkynediol of the formula VI

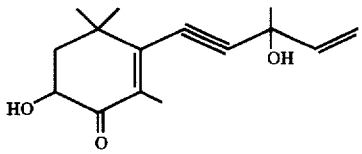

(VI)

with zinc dust in methylene chloride/acetic acid,

D. reacting the resulting $C_{15}$-diol of the formula IV

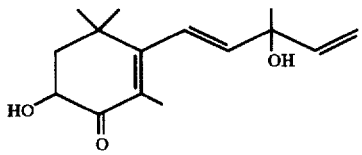

(IV)

with hydrochloric or hydrobromic acid,

E. reacting the resulting $C_{15}$-halide of the formula VII

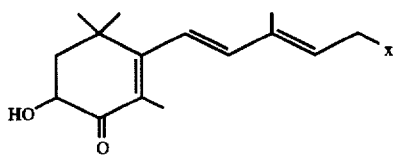

(VII)

where x is Cl or Br, with triphenylphosphine, and

F. subjecting the resulting triphenylphosphonium salt of the formula VIII

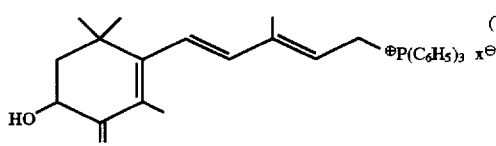

(VIII)

to a Wittig reaction with 2,7-dimethyl-2,4,6-octa-trienedial to give astaxanthin.

EXAMPLE 1 a. Preparation of the $C_9$ unit 170 g (1.0 mol) of crystalline 3,4-dihydroxy-2,6,6-trimethyl-2-cyclohexen-1-one were suspended in 500 ml of methylene chloride. First 500 mg (2.9 mmol) of p-toluenesulfonic acid were added to the suspension and then 144 g (2.0 mol) of vinyl ethyl ether were run in at room temperature (RT) over the course of 2 hours (h). The mixture was then stirred at RT for 4 h and subsequently 100 ml of 5% strength sodium hydroxide solution were run in. The lower organic phase was separated off, and the aqueous phase was extracted once with 100 ml of methylene chloride. The combined organic phases were washed with 200 ml of water and concentrated in a rotary evaporator. The residue was dried under greatly reduced pressure (oil pump) to give 2,4,6,6-tetramethyl-7,7a-dihydro-6H-benzo[1,3]dioxol-5-one as a yellow oil which was pure by thin-layer chromatography (TLC) and almost pure by gas chromatography (GC).

The crude product was purified by distillation (at 90° C./0.1 mbar).

The yield was 185 g, corresponding to 94.4% of theory.

b Preparation of the $C_{15}$ unit of the formula I 118 g (5.13 mol) of solid lithium emide were added to 2.0 liters of methyl tert-butyl ether (MTB) and the colorless suspension was stirred at +50° C. for 30 minutes (min). Subsequently 840.g (5.0 mol) of 3-(1-ethoxyethoxy)-3-methyl-1-penten-4-yne were run in over the course of 30 min, and the mixture was stirred at +50° C. for 2 h. It was cooled to +25°–30° C. and then 558 g (2.85 mol) of the $C_9$ unit from Example 1a were run-in over the course of 15 min. The mixture was stirred at RT for 1.5 h and then run over the course of 15 min into a second vessel containing 1.5 l of water. The phases were stirred for 10 min. The aqueous phase- (lower) was separated off. The organic phase was washed three times with 500 ml of water each time and concentrated in a rotary evaporator with the bath at +50° C. under a pressure down to 150 mbar.

Residue from evaporation: 1435 g

Excess 3-(1-ethoxyethoxy)-3-methyl-1-penten-4-yne was removed by Sambay distillation (jacket temperature 110° C., 2–3 mbar, boiling point 40°–45° C.). Sambay discharge: 1023 g of 5-[3-(1-Ethoxyethoxy)-3-methylpent-4-en-1-ynyl]-2,4,6,6-tetramethyl-5,6,7,7a- tetrahydrobenzo[1,3] dioxol-5-ol with a purity of 95%.

c. Preparation of 6-hydroxy-3- (3-hydroxy-3-methyl-4-penten-1-ynyl)-2,4,4-trimethyl-2-cyclohexen-1-one (VI)

603 g (1.65 mol) of the tertiary alcohol of the formula I obtained in 1b (Sambay discharge) were dissolved in 1400 ml of $CH_2Cl_2$. To this were added 500 ml of water and then 250 ml of 30% strength $H_2SO_4$, and the mixture was stirred at RT overnight. The organic phase (lower) was separated off and washed once each with 500 ml of 5% strength $NaHCO_3$ solution and 500 ml of water.

The organic phase was concentrated in a rotary evaporator and the oily residue was dried under greatly reduced pressure.

Weight: 408 g of 6-hydroxy-3-(3-hydroxy-3-methyl-4-penten-1-ynyl)-2,4,4-trimethyl-2-cyclohexen-1-one corresponding to a quantitative crude yield.

d. Preparation of the triphenylphosphonium salt of the formula VIII 248 g (1 mol) of the crude alkynediol of the formula VI prepared as in Example 1c were dissolved in 1000 ml of methylene chloride. After cooling to 0° C., 180 g (3.0 mol) of acetic acid were run in. Then, at 0° C., 11 g portions of zinc powder were added at 15-min intervals (in total 88 g of zinc corresponding to 1.35 g atom). After the last addition of zinc the mixture was stirred at 0° C. for 45 min. The resulting zinc acetate was filtered off, and the filter cake was washed twice with 250 ml of methylene chloride each time. To the filtrate at 0° C. were added over the course of 15 min 258 g of a 47% strength aqueous solution of HBr (1.50 mol HBr), and the mixture was then stirred at 0° C. for 20 min. 900 ml of water were then run in and the organic phase (lower) was separated off. The aqueous phase was washed once with 150 ml of methylene chloride. The combined organic phases were mixed with 900 ml of water. 47 g of solid NaHCO₃ were added and the phases were then stirred for a few min. The lower phase was separated off and washed with 900 ml of water, and 8 ml of 1,2-epoxybutane were added. While cooling to ≦10° C., 262 g (1.0 mol) of solid triphenylphosphine were added in portions over the course of about 15 min, the mixture was allowed to reach RT over the course of about 30 min, and a further 8 ml of 1,2-epoxybutane were added.

Subsequently, under atmospheric pressure, methylene chloride was distilled out while simultaneously running in MTB until a boiling point reached +55° C.

The triphenylphosphonium salt suspension was cooled to RT, stirred at RT for 30 min and filtered with suction. The filter cake was washed twice with 800 ml of MTB each time and dried under a stream of N₂ overnight.

Weight: 419 g (73% of theory)

EXAMPLE 2

Preparation of astaxanthin from alkynediol of the formula VI without isolation of the triphenylphosphonium salt of the formula VIII.

100 g of crude alkynediol of the formula VI (GC purity about 86%) were dissolved in 400 ml of methylene chloride. After cooling to 0° C., 72 g of acetic acid were run in. At 0° C., 4.4 g portions of zinc powder were added at 15-min intervals (in total 35.2 g of zinc). After the last addition of zinc, the mixture was stirred at 0° C. for 45 min. The resulting zinc acetate was filtered off, and the filter cake was washed twice with 70 ml of methylene chloride each time. The filtrate was washed twice with 300 ml of water each time and added dropwise over the course of 30 min to 104 g of 47% strength aqueous HBr at 0° C. The mixture was stirred at 0° C. for 30 min, 360 ml of water were run in, and the organic phase was separated off. The aqueous phase was extracted once with 50 ml of methylene chloride. The combined organic phases were mixed with 360 ml of water. 47 g of solid NaHCO₃ were added and the phases were then briefly stirred together. The lower phase was separated off and washed with 360 ml of water, and 3 ml of 1,2-epoxybutane were added. While cooling to ≦+10° C., 105 g of triphenylphosphine were added, and the mixture was stirred at RT for 18 h. Then 22.8 g (0.139 mol) of the C10-dialdehyde 2,7-dimethyl-2,4,6-octatrienedial were added, the mixture was cooled to 0° C. and, at 0° C., 57.5 g of a 30% strength methanolic sodium methylate solution were run in. The mixture was stirred at 0° C. for 3 h and then 500 ml of water were added. The organic phase was separated off, and the aqueous phase was extracted twice with 100 ml of methylene chloride each time. The combined organic phases were washed once with 400 ml of water. Under atmospheric pressure, methylene chloride was distilled out while simultaneously running in methanol until the boiling point was +65° C. The suspension was refluaced for 15 h and then cooled to 0° C. The resulting crystals were filtered off, washed with methanol and heptane and then taken up in 500 ml of methylene chloride. The solvent was replaced by methanol again as described above. The filter cake was dried to afford 63 g (76.0% of theory) of astaxanthin with a purity of 98.2% according to HPLC.

We claim:

1. A process for preparing astaxanthin of the formula V,

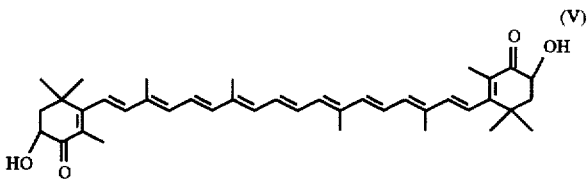

which comprises

A. reacting an alkenyne of the formula II

where $R^3$ is an ether, or acetal protective group which can be converted into a hydroxyl group by hydrolysis, in an inert solvent in the presence of lithium amide with a cyclohexenone of the formula III

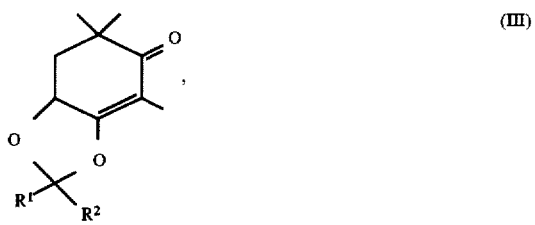

where $R^1$ is H or $C_1$–$C_4$-alkyl and $R^2$ is $C_1$–$C_4$-alkyl,

B. eliminating from the resulting tertiary alcohol of the formula I

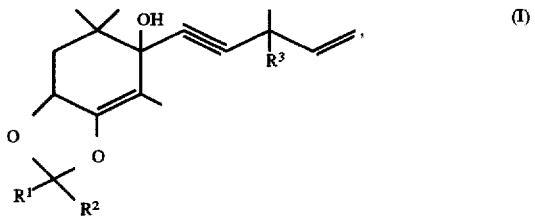

the protective groups in aqueous acidic medium,

C. reducing the resulting alkynediol of the formula VI

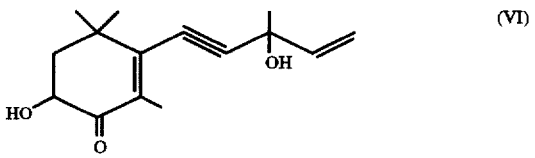

with zinc dust in methylene chloride/acetic acid,

D. reacting the resulting $C_{15}$-diol of the formula IV

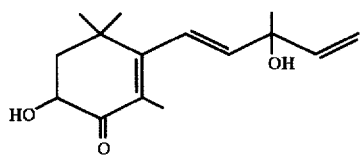
(IV)

with hydrochloric or hydrobromic acid,

E. reacting the resulting halide of the formula VII

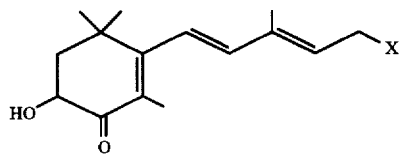
(VII)

where x is Cl or Br, with triphenylphosphine, and

F. subjecting the resulting triphenylphosphonium salt of the formula VIII

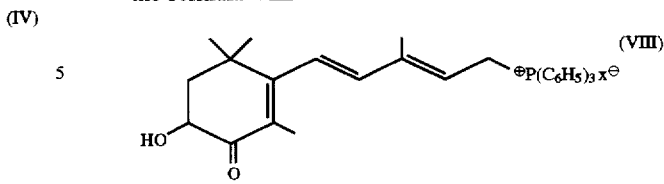
(VIII)

where x is Cl or Br, to a Wittig reaction with 2,7-dimethyl-2,4,6-octa-trienedial to give astaxanthin.

2. A process for preparing astaxanthin of the formula V as claimed in claim 1, wherein stages C., D., E. and F. are carried out without isolating the intermediates of the formula IV, VII and VIII.

* * * * *

UNITED STATES PATENT AND TRADEMARK OFFICE
CERTIFICATE OF CORRECTION

PATENT NO.: 5,625,099

DATED: April 29, 1997

INVENTOR(S): ERNST et al.

It is certified that error appears in the above-identified patent and that said Letters Patent is hereby corrected as shown below:

Column 12, claim 1, line 11, "Witrig" should be --Wittig--.

Signed and Sealed this

Eighth Day of July, 1997

Attest:

BRUCE LEHMAN

*Attesting Officer*

*Commissioner of Patents and Trademarks*